(12) United States Patent  
Lim et al.

(10) Patent No.: US 7,087,055 B2
(45) Date of Patent: Aug. 8, 2006

(54) MINIMALLY INVASIVE EXPANDING SPACER AND METHOD

(75) Inventors: Roy Lim, Germantown, TN (US); Michael C. Sherman, Memphis, TN (US); Kevin T. Foley, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 620 days.

(21) Appl. No.: 10/178,960

(22) Filed: Jun. 25, 2002

(65) Prior Publication Data

US 2003/0236520 A1 Dec. 25, 2003

(51) Int. Cl.
*A61B 17/70* (2006.01)

(52) U.S. Cl. .................... 606/61; 606/90; 606/198; 623/17.16

(58) Field of Classification Search ............... 606/61, 606/69, 70, 71, 90, 105, 198, 205, 207, 208; 623/17.16; 433/7; 33/302–304, 512, 613, 33/645; 600/222, 224

See application file for complete search history.

(56) References Cited

U.S. PATENT DOCUMENTS

| | | | |
|---|---|---|---|
| 3,550,636 A * | 12/1970 | Hearne et al. .............. 138/89 |
| 5,171,278 A | 12/1992 | Pisharodi | |
| 5,235,966 A | 8/1993 | Jamner | |
| 5,390,683 A | 2/1995 | Pisharodi | |
| 5,522,899 A | 6/1996 | Michelson | |
| 5,599,279 A | 2/1997 | Slotman et al. | |
| 5,620,458 A | 4/1997 | Green et al. | |
| 5,658,335 A | 8/1997 | Allen | |
| 5,665,122 A | 9/1997 | Kambin | |
| 5,695,515 A * | 12/1997 | Orejola ................. 606/191 |
| 5,697,889 A | 12/1997 | Slotman et al. | |
| 5,782,832 A | 7/1998 | Larsen et al. | |
| 5,865,848 A | 2/1999 | Baker | |
| 5,888,224 A | 3/1999 | Beckers et al. | |
| 6,039,761 A | 3/2000 | Li et al. | |
| 6,045,579 A | 4/2000 | Hochshuler et al. | |
| 6,080,193 A | 6/2000 | Hochshuler et al. | |
| 6,102,950 A | 8/2000 | Vaccaro | |
| 6,126,689 A | 10/2000 | Brett | |
| 6,127,597 A | 10/2000 | Beyar et al. | |
| 6,174,334 B1 | 1/2001 | Suddaby | |
| 6,176,882 B1 | 1/2001 | Biedermann et al. | |
| 6,179,873 B1 | 1/2001 | Zientek | |

(Continued)

FOREIGN PATENT DOCUMENTS

DE 200 04 812 U1 11/2000

(Continued)

*Primary Examiner*—David O. Reip
(74) *Attorney, Agent, or Firm*—Coats & Bennett, P.L.L.C.

(57) ABSTRACT

A minimaly invasive spacer for positioning between vertebral members. The spacer is adjustable between a first orientation having a reduced size to facilitate insertion between the vertebral members. A second orientation has an enlarged size for contacting the vertebral members. The spacer includes linkages that are attached to a pair of plates. A pull arm is operatively connected to the linkages for adjusting the spacer from the first orientation to the second orientation. A delivery device is attached to the spacer for insertion between the vertebral members. In one embodiment, the delivery device is detachable to be removed from the spacer once positioned between the vertebral members. Methods of using the spacer include positioning the spacer between the vertebral members while in the first orientation. The spacer is then enlarged to the second orientation, and the delivery device is removed with only the spacer remaining within the patient.

46 Claims, 4 Drawing Sheets

| U.S. PATENT DOCUMENTS | | | |
|---|---|---|---|
| 6,183,517 B1 | 2/2001 | Suddaby | |
| 6,190,414 B1 | 2/2001 | Young et al. | |
| 6,193,757 B1 | 2/2001 | Foley et al. | |
| 6,217,579 B1 | 4/2001 | Koros | |
| 6,332,895 B1 | 12/2001 | Suddaby | |
| 6,582,451 B1 * | 6/2003 | Marucci et al. | 606/207 |
| 2003/0220650 A1 * | 11/2003 | Major et al. | 606/90 |

| FOREIGN PATENT DOCUMENTS | | |
|---|---|---|
| EP | 0 676 176 A1 | 10/1995 |
| WO | WO 95/25485 | 9/1995 |
| WO | WO 97/00054 | 1/1997 |
| WO | WO 01/41652 | 6/2001 |

* cited by examiner

MINIMALLY INVASIVE EXPANDING SPACER AND METHOD

BACKGROUND

Various devices are used for controlling the spacing between vertebral members. These devices may be used on a temporary basis, such as during surgery when it is necessary to access the specific surfaces of the vertebral member. One example includes preparing the endplates of a vertebral member. The devices may also remain permanently within the patient to space the vertebral members.

It is often difficult to position the device between the vertebral members in a minimally invasive manner. A device that is small may be inserted into the patient and between the vertebral members in a minimally invasive manner. However, the small size may not be adequate to effectively space the vertebral members. A larger device may be effective to space the vertebral members, but cannot be inserted into the patient and between the vertebral members in a minimally invasive manner.

SUMMARY

The present invention is directed to a minimally invasive spacer for spacing vertebral members. The spacer is positionable between a closed orientation to fit between the vertebral members. The spacer may be expanded to a variety of sizes larger than the closed orientation to space the vertebral members as desired. In one embodiment, the spacer may be locked in the open configuration.

The spacer is a mechanical device having a pair of plates that contact the vertebral members. In one embodiment, both plates move outward from a centerline of the device. In another embodiment, only one of the plates moves outward from the centerline.

Linkages are positioned between and pivotally attached to the plates. A link angle is formed by the linkages and the centerline of the device. The linkages move from a closed orientation having a first link angle to a variety of open orientations each having a link angle greater than the first link angle.

In one embodiment, linkages are paired together between the plates. A first end of the linkages is attached to the first plate, and a second end is attached to the second end. The linkages are attached together about the centerline of the device. In one embodiment, a complimentary pair of linkages are adjacently positioned to the first link pair. The complimentary linkage pairs may each include toothed-ends that mate together when the spacer moves from the closed orientation to the open orientation.

A pull arm is positioned within the spacer to apply an axial force to the linkages. The pull arm is pivotally connected to the linkages. As the pull arm moves, linkages that are pivotally connected move outward thus increasing the height of the spacer. A variety of different devices may be used for applying an axial force to the pull arm.

A delivery device may be used for positioning the spacer between the vertebral members. The delivery device may be permanently attached to the spacer such that both the spacer and delivery device are removed after completion of the procedure. In another embodiment, the delivery device is removably connected to the spacer and can be removed from the patient leaving the spacer between the vertebral members. In one embodiment, the delivery device may be reattachable to the spacer. Once delivered between the vertebral members and the spacer is deployed, the delivery device may be disconnected and removed to give the surgeon more space. Once completed with the procedure, the delivery device may be reattached to remove the spacer. Prior to removal, the spacer may be returned towards the closed orientation.

DETAILED DESCRIPTION

Figure 1:
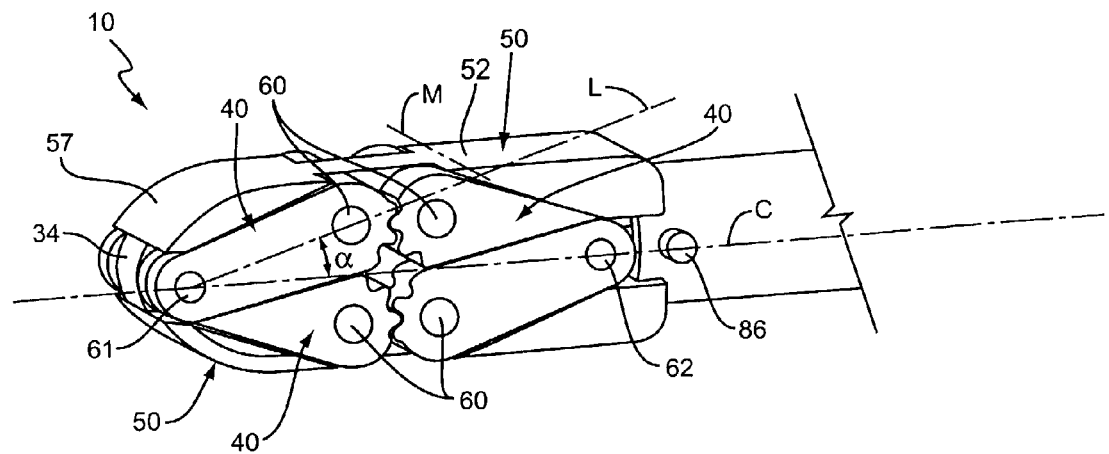
FIG. 1 is a perspective view of a spacer in a closed orientation according to one embodiment of the present invention.
Figure 2:
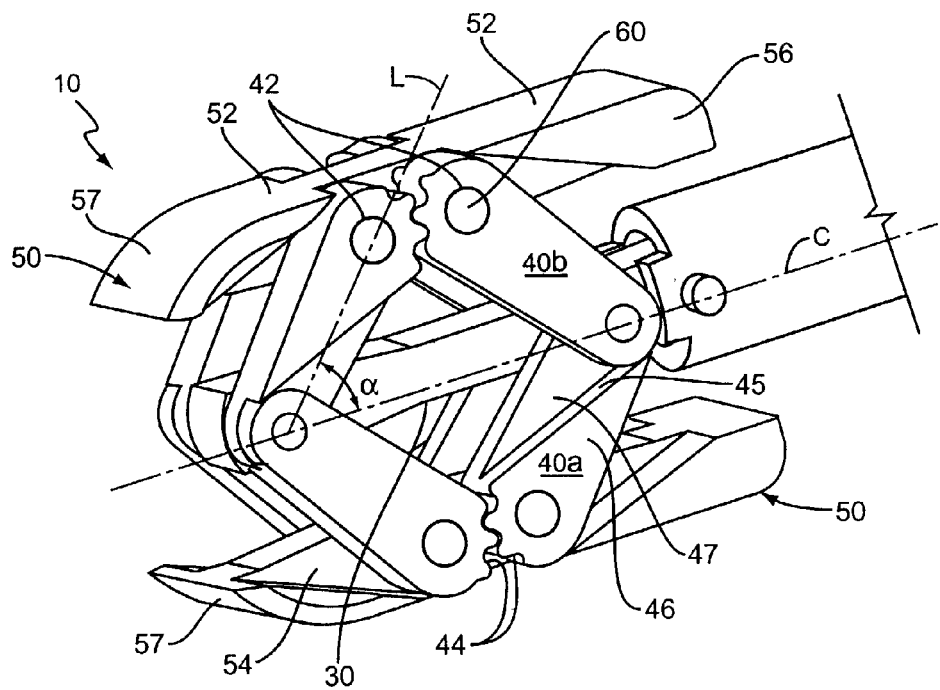
FIG. 2 is a perspective view of a spacer in an opened orientation according to one embodiment of the present invention.

The present invention is directed to a minimally invasive spacer, generally illustrated as 10, for positioning between vertebral members. The spacer 10 is adjustable between a variety of sizes between a first orientation and a second orientation. The first orientation is illustrated in FIG. 1 and has a reduced size to facilitate insertion into the patient and between the vertebral members. A second orientation, as illustrated in FIG. 2, has an enlarged size for contacting and spreading the vertebral members. The spacer 10 includes linkages 40 attached to a pair of plates 50. A pull arm 30 operatively connects to the linkages 40 to adjust the spacer 10 at positions between the first orientation and the second orientation. A delivery device 80 is attached to the spacer 10 to deliver the spacer 10 between the vertebral members. The delivery device 80 may be detachable to be removed from the spacer 10 once positioned between the vertebral members.

Spacer 10 may include a number of linkages 40 positioned between the plates 50 depending upon the application. Each individual linkage 40 mates with a complimentary linkage 40 to provide movement to the spacer 10. In embodiments illustrated in FIGS. 1 and 2, spacer 10 includes two pairs of linkages 40 on a first side of the pull arm 30, and another two pairs of linkages 40 on a second side of the pull arm 30 for a total of four pairs of linkages, or eight total linkages. In another embodiment (not illustrated), spacer 10 includes only two pairs of linkages 40, or four total linkages. Various numbers of linkages 40 may be included within the present invention depending upon the specific requirements of the spacer and necessary amount of disc space load. In one embodiment, linkages 40 are independent and individually spaced apart. In another embodiment, linkages 40 are paired together, but adjacent linkage pairs do not contact.

Figure 6:
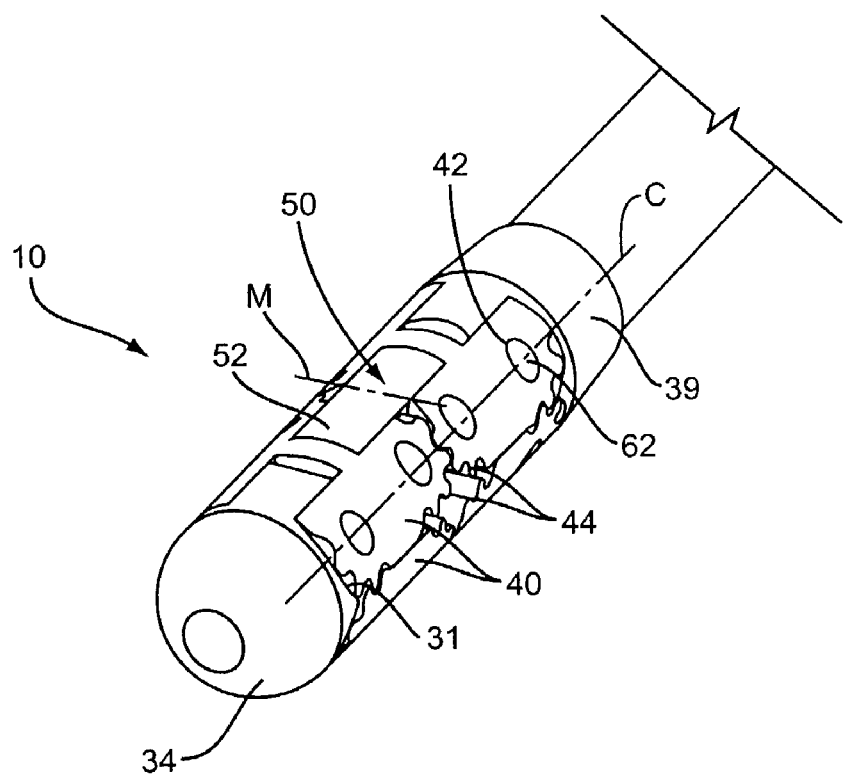
FIG. 6 is a perspective view of another embodiment of the spacer in a closed orientation.
Figure 7:
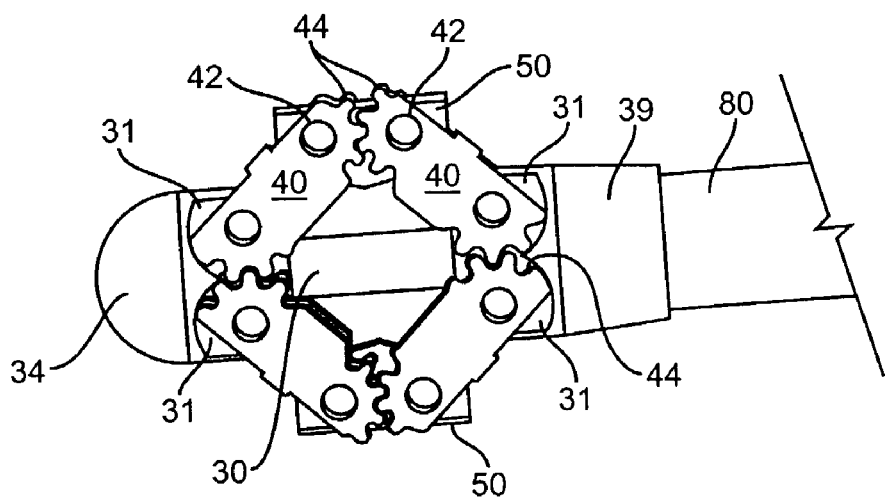
FIG. 7 is a perspective view of another embodiment of the spacer in an open orientation.

Each linkage 40 has an elongated shape with an aperture 42 adjacent to each end to receive pins. The ends of each linkage 40 may have a variety of shapes and configurations. In embodiments illustrated in FIGS. 1 and 2, each end is substantially rounded. In the embodiments illustrated in FIGS. 6 and 7, each end has a partially rounded section with a linear edge extending along one side of the linkage 40. In one embodiment, teeth 44 are positioned about at least one end of each linkage 40. Teeth 44 are sized to mate with complimentary teeth 44 on adjacent linkages 40. Teeth 44 may be positioned along the ends of the linkages 40, or may also extend along the elongated length. In the embodiments illustrated in FIGS. 1 and 2, teeth 44 are positioned along one side of the rounded edge. In the embodiments of FIGS. 6 and 7, teeth 44 extend along only a section of each end and further down along the length.

In one embodiment, linkages 40 are shaped to compliment adjacent linkages. In one embodiment illustrated in FIG. 2, a linkage first side 40a includes a recessed section 47 and an extended section 46. An edge 45 extends across the length of the linkage 40 defining the recessed section 47 and extended section 46. A linkage second side 40b may have a variety of configurations, such as substantially flat. The linkages 40 overlap with the first sides 40a mating together in the closed orientation. The complimentary shapes give the linkages 40 a smaller profile thus reducing the dimensions of the spacer 10 as illustrated in FIG. 1.

Plates 50 are positioned on a first and second side of the spacer 10 to contact the vertebral members. Plates 50 include a contact surface 52 having a surface area to distribute the disc space load created by the spacer 10 across a large region of the vertebral members. In one embodiment, the contact surface 52 is about 16 mm in length by about 8 mm in width. The dimensions of the contact surface 52 may vary depending upon the construction of the spacer 10. By way of example, embodiments illustrated in FIGS. 1 and 2 have a contact surface 52 with a substantially hourglass shape. In embodiments illustrated in FIGS. 6 and 7, contact surface 52 has a substantially rectangular shape. In embodiments illustrated in FIGS. 1 and 2, the contact surface 52 is substantially flat. In another embodiment, the contact surface 52 may be rounded. In one embodiment, plate 50 has a width equal to the overall width of the spacer 10. In another embodiment, plate 50 has a width less than the overall width of the spacer 10.

Linkages 40 may connect to the plates 50 in a number of different positions. In one embodiment, an edge 56 of contact surface 52 has a width for receiving an aperture for receiving a pin. In embodiments illustrated in FIGS. 1 and 2, plates 50 include an outwardly extending rib 54. Rib 54 is sized with an aperture therein to receive the pin.

In one embodiment, plate 50 includes a front 57 which is angled or rounded inward relative to the contact surface 52. In one embodiment, front 57 has a length such that distal ends of the first and second plates 50 contact each other in the closed orientation. In another embodiment, front 57 extends a lesser distance to cover only a portion of the linkages 40 and pull arm 30 when in the closed orientation.

Figure 3:
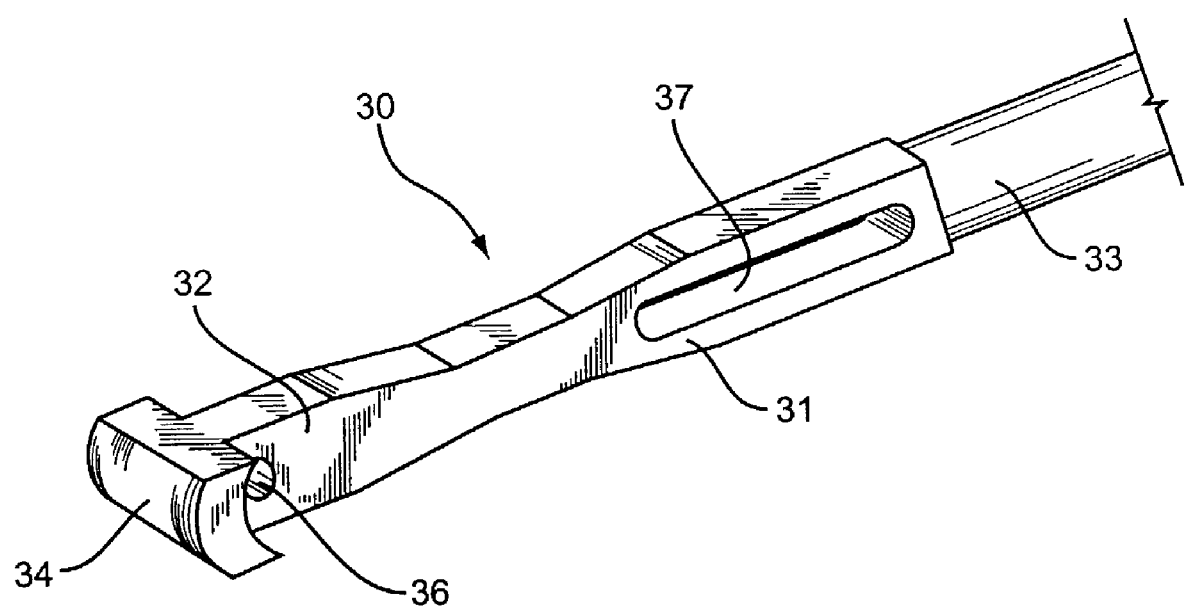
FIG. 3 is a perspective view of a pull arm according to one embodiment of the present invention.

Pull arm 30 moves the linkages 40 from the closed orientations through the open orientations. One embodiment of the pull arm 30 is illustrated in FIG. 3 and includes an elongated body having an aperture 36 and a slot 37 for receiving pins. A nose 34 on the distal end may have a rounded or angled shape. As illustrated in FIG. 1, the rounded or angled shape facilitates insertion of the spacer 10 between the vertebral members. In one embodiment as illustrated in FIG. 3, pull arm 30 includes a distal section 31 and a proximal section 33 that are detachable. When the device 80 is detached from the spacer 10, proximal section 33 detaches from the distal section 31. The spacer 10, including the pull arm distal section 31, remains as the delivery device 80 and proximal pull arm 33 are removed.

The pull arm 30 may extend through only a portion of the delivery device 80, or may extend through the entire length.

Pins are positioned within the spacer 10 to connect together the linkages 40, pull arm 30, and plates 50. As illustrated in FIG. 1, pins 60 extend through the linkages 40 and plate 50. Pin 61 extends through the linkages 40 and aperture 36 in the pull arm 30 at the distal end of the spacer. Pin 62 extends through the linkages 40 and slot 37 in the pull arm 30. Pins 60, 61, and 62 may have a variety of diameters and sizes depending upon the specific application of the spacer 10. In one embodiment, each pin has a diameter of about 1.33 mm. The term "pin" used herein is broadly used as a means for pivotally attached two or more members. One skilled in the art will understand that various other similar devices may serve this same function and are considered within the scope of the present invention.

As illustrated in FIG. 1, in the closed orientation the spacer 10 has a bullet-like configuration. The plates 50, linkages 40, and pull arm 30 combine together to form a rounded or angled front which eases the insertion of the spacer 10 in the patient. In one embodiment, the contact surfaces 52 are symmetric about a centerline C, i.e., have the same orientation relative to the centerline. In one embodiment, the contact surfaces 52 of the plates 50 are parallel with the centerline C when the spacer 10 is in the closed orientation. In one embodiment, the spacer 10 in the closed orientation has a length of between about 22–24 mm, width of about 8 mm, and a height of about 7 mm.

As illustrated in FIG. 2, the spacer 10 in the open configuration has a larger height. The height may be adjusted depending upon the angle of the linkages 40 relative to the centerline C. The spacer 10 may be expanded to a variety of different sizes and heights and the term "open configuration" is used to indicate any of these orientations. In one embodiment, when the spacer 10 is expanding from the closed orientation, the contact surfaces 52 remain symmetrical about the centerline C. In one embodiment, both plates 50 move equal amounts such that the distance between the centerline C and the contact surface is the same for each plate 50. In another embodiment, one plate 50 moves a greater amount than the corresponding plate 50. In another embodiment, one plate 50 is fixed and the corresponding plate 50 move outward to increase the height of spacer 10.

Figure 4:
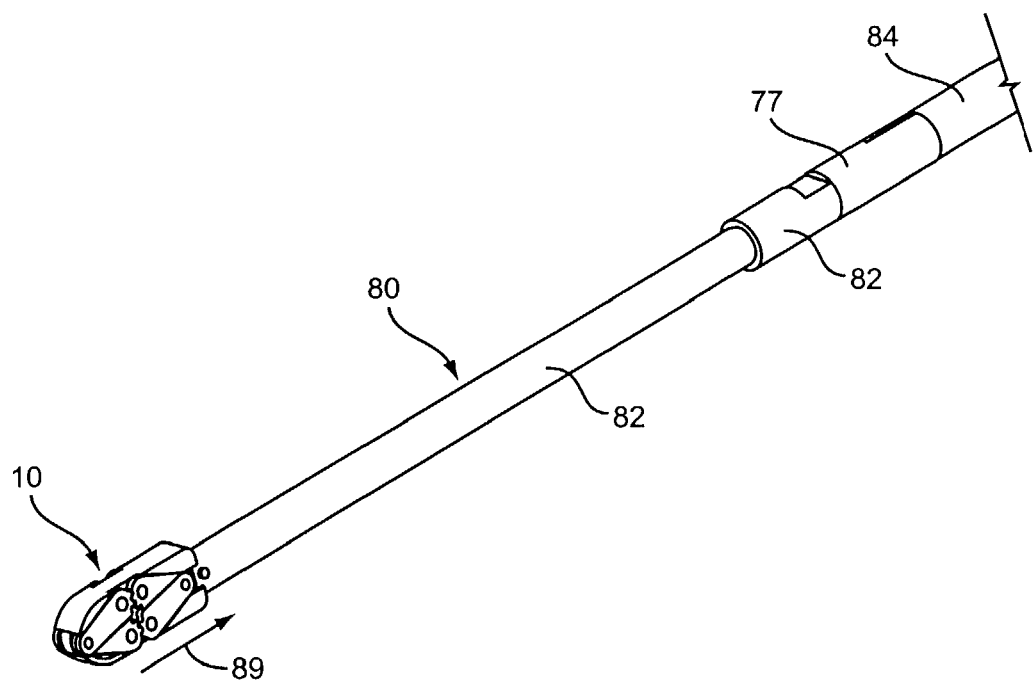
FIG. 4 is a is a perspective view of one embodiment of the spacer and attached delivery device constructed according to one embodiment of the present invention.

A variety of different delivery devices 80 may be used for positioning the spacer 10 between the vertebral members. One embodiment is illustrated in FIG. 4 and includes an elongated rod attached to the proximal end of the spacer 10. In one embodiment, the delivery device is hollow and surrounds at least a portion of the pull arm 30. Delivery device 80 may have a variety of cross-sectional shapes and sizes depending upon the application. Delivery device 80 may be constructed of a single elongated member, or may be constructed of different sections such as first section 82 and second sections 84.

Delivery device 80 may be attached to the spacer 10 in a number of different manners. In one embodiment as illustrated in FIG. 1, pin 86 extends through the device 80 and the slot 37 within the pull arm 30 to connect the spacer 10 to the device 80. In another embodiment, the delivery device 80 is permanently attached to the spacer 10. In another embodiment, the pull arm 30 is also the delivery device 80.

In one embodiment, the spacer 10 is inserted via the delivery device 80 between the vertebral members and removed upon completion of the procedure. In one embodiment, the spacer 10 is removed from the delivery device 80 and remains within the patient. The spacer 10 may remain permanently within the patient, or in one embodiment, after the spacer is detached and the surgeon completes the procedure, the delivery device 80 is reattached to remove the spacer 10. In one embodiment, pin 86 is broken to remove the device 80 from the spacer 10. In one embodiment as illustrated in FIG. 3, pull arm 30 includes a distal section 31 and a proximal section 33 that are detachable. When the device 80 is detached from the spacer 10, proximal section 33 detaches from the distal section 31. The spacer 10, including the pull arm distal section 31, remains as the device 80 and proximal pull arm 33 are removed.

In one manner of use, spacer 10 is connected to the distal end of the delivery device 80. While in the closed orientation, the spacer 10 is positioned within the patient between adjacent vertebral members. In one embodiment, the spacer 10 is positioned within the disc space between the adjacent vertebral members and contacts the end plates of the vertebral members upon expansion. Once positioned, an axial load or deployment force is applied to the pull arm 30 to force the pull arm 30 inward in the direction of arrow 89 in FIG. 4. Axial movement results in the linkages 40 pivoting outward from the closed position in the embodiment of FIG. 1 towards the open orientation in the embodiment of FIG. 2. The teeth 44 of opposing linkages 40 mate together during the movement with the plates 50 moving outward from the centerline C. In one embodiment, each of the two plates 50 move equal amounts and are symmetric about the centerline C.

As the linkages 40 expand outward and the pull arm 30 moves inward, pin 62 slides along the distal arm slot 37 as the spacer 10 moves from the closed to open orientations. Pin 61 is mounted within linkages 40 and the pull arm aperture 36 and does not move relative to the pull arm 30. In the closed orientation illustrated in FIG. 1, pin 61 is spaced apart from pin 62 a distance greater than in the open orientation as illustrated in FIG. 2. The amount of axial movement of the pull arm 30 results in the amount of deployment of the spacer 10. The spacer 10 may be opened to any distance between the closed and open orientations depending upon the specific application.

An axial force is applied to the pull arm 33 to deploy the spacer 10 to the open position. The power mechanism to apply the force may be within the spacer 10, or delivery device 80. In one embodiment, the axial force is applied by linearly moving the pull arm 30. In one embodiment, section 84 is attached to the proximal pull arm 33. The section 84 can be locked in the extended position away from the first section 82 to lock the spacer 10 in the open orientation. In one embodiment, a scroll 77 is threaded onto the distal end of the second section 84 adjacent to the first section 82 as illustrated in FIG. 4. Section 84 and scroll 77 are distanced from section 82 thereby applying force to the pull arm 30 and expanding the distractor 10 Scroll 77 can be threaded distally along the second section 84 to contact the first section 82 and lock the distractor 10 in an opened position. To close the distractor 10, scroll 77 is threaded proximally along the second section 84. In one embodiment, scroll 77 is knurled to allow rotation of the scroll 77 by hand.

Figure 5:
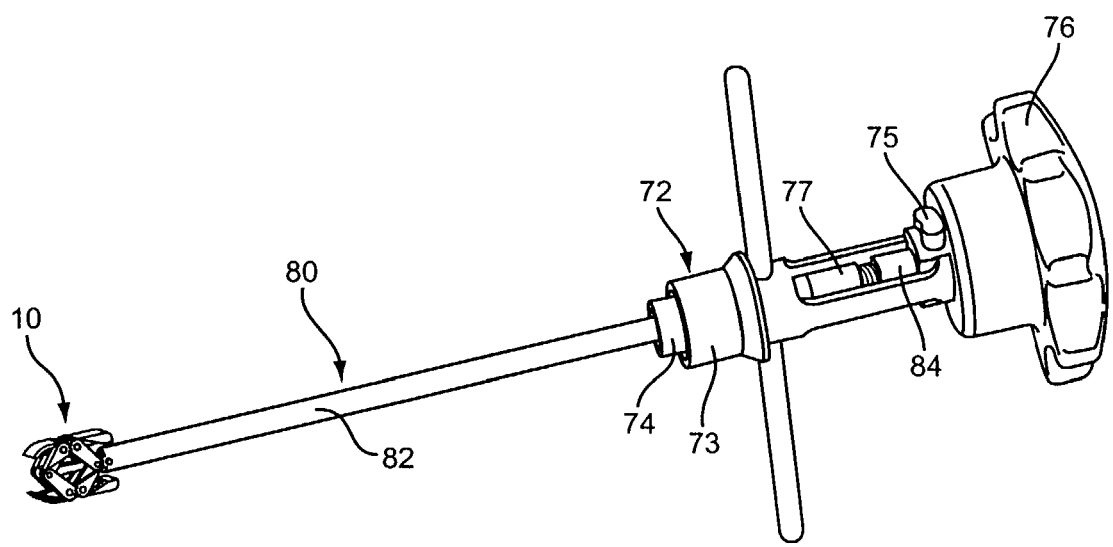
FIG. 5 is a perspective view of one embodiment of the spacer, delivery device, and force mechanism constructed according to one embodiment of the present invention.

A mechanism for applying an axial force to the pull arm 30 may have a variety of configurations. The mechanism may be positioned adjacent to the spacer 10, or positioned distant from the spacer 10 to be outside the patient. In one embodiment illustrated in FIG. 5, a power mechanism 70 is attached to the delivery device 80 to apply an axial force. Power mechanism 70 includes a quick release mechanism 72 at the distal end of power mechanism 70 to attach to the delivery device first section 82. In one embodiment, quick release mechanism 82 includes a spring-biased collar 73 positioned around a receptacle 74. Collar 73 may be pulled back to load the first section 82 within the receptacle 74. Releasing the collar 73 causes the receptacle 74 to contract and lock the first section 82. In one embodiment, quick release mechanism 82 includes one or more balls that engage in grooves in the first section 82. In one embodiment, a slide lock 75 attaches to the second section 84. Torque is applied to a handle 76 causing the scroll 77 and second section 84 to separate from the first section 82 thus applying an axial force to the pull arm 30 and opening the distractor 10. At the desired orientation, scroll 77 is threaded distally to contact the first section 82 and lock the distractor 10. Once locked, the power mechanism 70 can be removed from the delivery device 80 for more working space for the surgeon.

A linkage axis L is formed by the line extending through the linkage 40. In embodiments illustrated in FIGS. 1 and 2, linkage axis L extends through the points of intersection with the plate 50 and pull arm 30. A link angle $\alpha$ is formed by the linkage axis L and the centerline C. In the embodiment illustrated in FIG. 1, the link angle a is greater than zero when the spacer 10 is in the closed orientation. In one embodiment, a link angle $\alpha$ greater than 0° in the closed orientation has been determined to facilitate opening the spacer 10.

The axial force, or required deployment force, necessary to open the spacer 10 changes during the expansion process. Additionally, the force applied pacer 10 on the vertebral members during the expansion process, or allowable disc space load, changes during the expansion process. Stated in another manner using a 3-coordinate geometry having coordinates x, y, and z, the axial force is the force in the x direction and the vertebral member load is the force in the y direction.

In one embodiment, the spacer 10 is positionable between a closed orientation having a height of about 7 mm and a link angle $\alpha$ of about 16°, and an open configuration having a height of about 14 mm and a link angle $\alpha$ of about 49°. The following chart illustrates the parameters of the spacer 10 at the various stages of deployment:

| Height h (mm) | Link Angle $\theta$ rads | Link Angle $\theta$ (degrees) | Required Deployment Force (lbf) | Allowable Disc Space Load (lbf) |
|---|---|---|---|---|
| 7 | 0.29 | 16.61 | 541.15 | 322.79 |
| 7.5 | 0.33 | 18.63 | 535.12 | 360.76 |
| 8 | 0.36 | 20.67 | 528.34 | 398.74 |
| 8.5 | 0.40 | 22.75 | 520.77 | 436.71 |
| 9 | 0.43 | 24.85 | 512.40 | 474.69 |
| 9.5 | 0.47 | 27.00 | 503.17 | 512.66 |
| 10 | 0.51 | 29.18 | 493.04 | 550.64 |
| 10.5 | 0.55 | 31.41 | 481.94 | 588.61 |
| 11 | 0.59 | 33.70 | 469.82 | 626.59 |
| 11.5 | 0.63 | 36.05 | 456.59 | 664.56 |
| 12 | 0.67 | 38.47 | 442.15 | 702.54 |
| 12.5 | 0.72 | 40.97 | 426.38 | 740.51 |
| 13 | 0.76 | 43.57 | 409.11 | 778.49 |
| 13.5 | 0.81 | 46.30 | 390.17 | 816.46 |
| 14 | 0.86 | 49.16 | 369.28 | 854.44 |

These calculations are theoretical and based on the yield strength (2% elongation) of a 1.3 mm pin in double shear which is approximately 564.7 lbs. As can be seen, the required deployment force decreases as the link angle $\alpha$ increases, and the allowable vertebral member load increases as the link angle $\alpha$ increases.

FIGS. 6 and 7 illustrate another embodiment of the spacer 10. FIG. 6 illustrates the spacer 10 in a closed orientation. The overall shape of the spacer 10 is cylindrical and includes a nose 34 having a rounded front to ease insertion into the patient. The spacer 10 includes linkages 40, a pair of plates 50, and a pull arm 30 including the nose 34. A proximal section 39 forms part of the spacer 10. In one embodiment, plates 50 have a length less than the overall spacer length. Linkages 40 include teeth 44 at each end, and a pair of apertures 42 for receiving pins 62. Nose 34 and proximal section 39 include recesses 31 in which the linkages 40 are positioned. In one embodiment, linkages 40 and plates 50 have a rounded surface to conform to the cylindrical shape. In another embodiment, linkages 40 and plates 50 have a flat exterior surface. In the closed orienation, the link angle α is 0°.

FIG. 7 illustrates the spacer 10 in the opened orientation. Teeth 44 of opposing linkages 40 mate together as the spacer 10 opens. Nose 34 is connected to a pull arm 30. An axial force applied to the pull arm 30 forces the nose 34 inward towards the delivery device 80. The movement of the nose 34 causes the linkages 40 to move resulting in plates 50 moving outward from the centerline C of the spacer 10. The pull arm 30 may be axially moved a variety of distances to control the height of the spacer 10.

In embodiments illustrated in FIGS. 6 and 7, linkages 40 do not connect directly to the pull arm 30. Linkages 40 connect to the nose 34 which is connected to the pull arm 30. Movement of the nose 34 causes movement of the linkages 40. The proximal linkages 40 may or may not be directly or indirectly connected to the pull arm 30. In one embodiment, proximal linkages 40 are directly connected to the pull arm through pins.

In one embodiment, the linkages 40 connect to a middle section of the plates 50 adjacent to a mid-point M of the length. In another embodiment, linkages 40 connect to the plates 50 towards the ends distanced away from the midpoint M. In another embodiment, two linkages 40 connect at different positions along the plates 50 relative to the midpoint M (i.e., linkages 40 are not evenly spaced from the mid-point M). By way of example, a first linkage 40 connects at a position near the distal end of the plate 50 a distance x from the mid-point M, and a second linkage 40 connects adjacent to the mid-point of the plate 50 at a distance x less y from the mid-point. The plates 50 may be parallel to the centerline C, or angled in either direction relative to the centerline C.

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions. In one embodiment, spacer 10 is positioned within the disc space between adjacent vertebra. Plates 50 contact the end plates of the vertebra to space the vertebra as necessary. In one embodiment, the spacer 10 is inserted posteriorly in the patient. In another embodiment, the spacer 10 is inserted from an anteriorly into the patient. In another embodiment, the spacer is inserted laterally into the patient.

In another embodiment (not illustrated), spacer 10 includes only one moving plate 50. A first plate is attached to the linkages 40 and moves as discussed above. A second plate is stationary. The linkages 40 move outward from the stationary plate to expand the height of the spacer 10 to the open orientation. This embodiment may include any number of linkages 40 depending upon the desired spacing and strength requirements.

The present invention may be carried out in other specific ways than those herein set forth without departing from the scope and essential characteristics of the invention. In one embodiment, spacer 10 and delivery device 80 are constructed of stainless steel. The present embodiments are, therefore, to be considered in all respects as illustrative and not restrictive, and all changes coming within the meaning and equivalency range of the appended claims are intended to be embraced therein.

What is claimed is:

1. A device for spacing vertebral members comprising:
   a plurality of linkages each comprising an elongated shape with a first end and a second end, at least one end having teeth;
   a pull arm pivotally connected to the first end of each of the plurality of linkages; and
   a first plate connected to the second end of at least one of the plurality of linkages and a second plate connected to the second end of at least one of the plurality of linkages;
   the pull arm being positioned in a first orientation with the linkages having a first link angle, and a second orientation with the plurality of linkages having a second link angle, with the second link angle being greater than the first link angle.

2. The device of claim 1, wherein the device has a substantially bullet-shape in the first orientation with a narrow first end and a wider second end.

3. The device of claim 1, wherein the first plate and the second plate are symmetric about a centerline in both the first orientation and the second orientation.

4. The device of claim 3, wherein the pair of plates are parallel in both the first orientation and the second orientation.

5. The device of claim 1, wherein the first link angle is greater than 0°.

6. The device of claim 1, wherein one of the first plate and the second plate is positioned a greater distance outward from a centerline in the second orientation than in the first orientation.

7. The device of claim 1, wherein the pull arm comprises a rounded distal end.

8. The device of claim 1, wherein the pull arm comprises an elongated slot for receiving a pin for attaching the first end of at least one of the plurality of linkages.

9. The device of claim 1, wherein teeth are positioned at the second end of each of the plurality of linkages.

10. The device of claim 9, wherein the teeth are positioned at the first end of each of the plurality of linkages.

11. The device of claim 1, wherein the pull arm is positioned between at least two of the plurality of linkages.

12. The device of claim 1, further comprising an elongated delivery device to position the device between the vertebral members.

13. The device of claim 12, wherein the elongated delivery device comprises a distal section and a proximal section with the pull arm being operatively connected to the proximal section and the distal section being separable from the proximal section.

14. The device of claim 13, further comprising a scroll positioned between the distal section and the proximal section, the scroll being movably attached to the proximal section.

15. The device of claim 12, wherein the elongated delivery device is detachable from the device.

16. The device of claim 1, further comprising a force mechanism operatively attached to the pull arm to apply an axial force, the force mechanism comprising a locking mechanism to attach to the elongated delivery device.

17. The device of claim 1, wherein outer surfaces of the first and second plates extend beyond the plurality of linkages to contact the vertebral members.

18. The device of claim 1, wherein the first plate and the second plate are each wider than the plurality of linkages.

19. The device of claim 1, wherein a distal end of the pull arm is positioned further inward relative to the first and second plates in the second orientation than in the first orientation.

20. A device for spacing vertebral members comprising:
a first plate and a second plate;
a pull arm; and
a first linkage and a second linkage each having a first end and a second end, each of the first ends being pivotally connected to the pull arm, the second end of the first linkage being pivotally connected to the first plate, and the second end of the second linkage pivotally connected to the second plate;
the first linkage and the second linkage being positionable between a first orientation and a second orientation, a distance between the second ends being less in the first orientation than in the second orientation;
wherein each of the first linkage and the second linkage comprise teeth on the first ends that mate together when moving between the first orientation and the second orientation.

21. The device of claim 20, wherein the first linkage and the second linkage overlap in the first orientation.

22. The device of claim 21, wherein the first linkage and the second linkage each include recessed sections that mate together in the first orientation.

23. The device of claim 20, wherein the pull arm is positioned parallel with a device centerline.

24. The device of claim 20, wherein the first and second linkages are positioned completely between the first and second plates in both the first and second orientations.

25. A device for spacing vertebral members comprising:
a first plate and a second plate;
a first linkage pair pivotally attached to the first plate and the second plate;
a second linkage pair pivotally attached to the first plate and the second plate;
when a distance between the first plate and the second plate changes, a first toothed end of the first linkage pair attached to the first plate mates with a first toothed end of the second linkage pair, and a second toothed end of the first linkage pair attached to the second plate mates with a second toothed end of the second linkage pair when a distance between the first plate and the second plate increases.

26. The device of claim 25, wherein each of the first linkage pair and the second linkage pair comprises a first link member and a second link member pivotally connected together.

27. The device of claim 25, wherein a total of four linkage pairs are positioned between the first plate and the second plate.

28. A device for spacing vertebral members comprising:
a first plate;
a second plate;
a pull arm positioned between the first plate and the second plate;
a first linkage pair and a second linkage pair each comprising a first end connected to the first plate, a second end connected to the second plate, the first linkage pair connected to the pull arm at a first connection point, and the second linkage pair connected to the pull arm at a second connection point;
the device positionable between a first orientation having a first height and a second orientation having a second height greater than the first height, a distance between the first connection point and the second connection point being greater in the first orientation than in the second orientation;
the first ends each having teeth that mate together as the device moves between the first orientation and the second orientation.

29. The device of claim 28, wherein the pull arm further comprises an elongated slot sized to receive a pin to attach the second linkage pair to the pull arm, the pin positioned at a first position within the elongated slot at the first orientation, and a second position within the elongated slot at the second orientation.

30. The device of claim 29, wherein the first linkage pair is statically connected to the pull arm with the first connection point being at the same position relative to the pull arm at the first orientation and the second orientation.

31. A method of spacing vertebral members comprising the steps of:
inserting a spacer in a first orientation with a first height between the vertebral members;
applying an axial force in a proximal direction to a pull arm to axially move the pull arm; and
pivoting linkages attached to the pull arm and increasing the spacer to a second height larger than the first height.

32. The method of claim 31, wherein the step of pivoting the linkages comprises moving the linkages from a first link angle to a second larger link angle.

33. The method of claim 31, wherein the step of pivoting the linkages causes one of first and second plates to move outward from a centerline of the spacer to increase the spacer from the first height to the second height with first and second plates contacting the vertebral members.

34. The method of claim 31, further comprising contacting the vertebral members with first and second plates in the second orientation as the linkages are positioned away from the vertebral members.

35. The method of claim 31, further comprising moving a pull arm in a proximal direction relative to a first plate during movement from the first orientation to the second orientation.

36. A method of spacing vertebral members comprising the steps of:
positioning a spacer between the vertebral members, the spacer being in a first orientation with a first height and a linkage having a first link angle; and
expanding the spacer from the first orientation to a second orientation with a second height greater than the first height and a second link angle greater than the first link angle;
with a distance between first attachment points between first and second linkages with a pull arm being greater in the first orientation than in the second orientation, and second attachment points between the first and second linkages with a plate being equal in both the first and second orientations.

37. A method of spacing vertebral members comprising the steps of:
  inserting a spacer between the vertebral members;
  applying an axial force to move a pull arm in a proximal direction;
  pivoting at least one pair of linkages from a first orientation having a first link angle to a second orientation having a second link angle greater than the first link angle; and
  moving a pair of plates from the first orientation sized to fit between the vertebral members to a second orientation having a height greater than the first orientation to contact the pair of plates against the vertebral members.

38. The method of claim 37, further comprising mating together teeth positioned at ends of the one pair of linkages when pivoting from the first orientation to the second orientation.

39. The method of claim 37, further comprising determining a distance between vertebral members based on the positioning of the pair of plates in the second orientation.

40. A method of spacing vertebral members comprising the steps of:
  inserting a spacer between the vertebral members, the spacer being in a closed orientation and having a closed height;
  applying a first deployment force and moving an arm in a proximal direction to move the spacer from the closed orientation to a first opened orientation and increasing the spacer to a first height larger than the closed height; and
  applying a second deployment force less than the first deployment force and moving the spacer from the first opened orientation to a second opened orientation and increasing the spacer to a second height greater than the first height.

41. The method of claim 40, further comprising increasing a link angle from a first angle to a greater second angle when moving the spacer from the closed orientation to the second opened orientation.

42. The method of claim 41, further comprising positioning the first angle to be greater than zero degrees.

43. A method of spacing vertebral members comprising the steps of:
  positioning a spacer between the vertebral members;
  applying a deployment force in a proximal direction;
  pivoting a pair of linkages each attached to a pull arm;
  separating a pair of plates from a first orientation having a first height to a second height greater than the first height; and
  applying a disc space load to the vertebral members, the disc space load being greater at the second height than at the first height.

44. The method of claim 43, wherein the step of applying the deployment force comprises applying an axial force to a pull arm that is operatively connected to the pair of linkages.

45. The method of claim 43, further comprising pivoting the pair of linkages from a first link angle in the first orientation to a second link angle in the second orientation, the second link angle being greater than the first link angle.

46. The method of claim 43, further comprising maintaining the pair of linkages between the pair of plates in both first and second orientations.

* * * * *